United States Patent [19]

Taniguchi et al.

[11] Patent Number: 5,077,205
[45] Date of Patent: Dec. 31, 1991

[54] METHOD FOR PREPARING CELLOBIOSE

[75] Inventors: Hajime Taniguchi, Ushiku; Takashi Sasaki; Motomitsu Kitaoka, both of Tsukuba, all of Japan

[73] Assignees: Keiji Umeda, Ibaraki; Nippon Petrochemicals Co., Ltd., Tokyo, both of Japan

[21] Appl. No.: 598,242

[22] Filed: Oct. 16, 1990

[30] Foreign Application Priority Data

Oct. 17, 1989 [JP] Japan .................................. 1-268171

[51] Int. Cl.$^5$ ...................... C12P 19/24; C12P 39/00; C12P 19/12
[52] U.S. Cl. ........................................ 435/94; 435/42; 435/100
[58] Field of Search ............................ 435/42, 94, 100

[56] References Cited

U.S. PATENT DOCUMENTS 4,410,627 10/1983 Lloyd et al. ........................... 435/94
4,683,203 1/1986 Yoshioka et al. ..................... 435/94

OTHER PUBLICATIONS

ABS APS J63146800, J63-49100, Katayama et al., pub. date ABS. 7-1988.

Primary Examiner—Herbert J. Lilling
Attorney, Agent, or Firm—Scully, Scott, Murphy & Presser

[57] ABSTRACT

A method for preparing cellobiose from sucrose in a high yield at low cost without difficulty by using three enzymes of sucrose phosphorylase, glucose isomerase and cellobiose phosphorylase in the presence of orthophosphate. The additional method of the invention comprises 4 steps: to treat sucrose with sucrose phosphorylase in the presence of orthophosphate to produce fructose and glucose-1-phosphate; to treat the fructose obtained in the preceding step with glucose isomerase to produce glucose; to treat the glucose obtained in the preceding step and the glucose-1-phosphate obtained in the first step with cellobiose phosphorylase to produce cellobiose and orthophosphate; and to recover at least a part of cellobiose from the reaction mixture in the preceding step and to recycle at least a part of the remaining reaction mixture containing orthophosphate to the first step.

4 Claims, 1 Drawing Sheet

METHOD FOR PREPARING CELLOBIOSE

BACKGROUND OF THE INVENTION

(1) Field of the Invention

The present invention relates to a novel method for preparing cellobiose. The cellobiose is a disaccharide which consists of two molecules of glucose connected by way of $\beta$-1,4 linkage and it is known as a smallest constituent unit of cellulose. This cellobiose is more stable as compared with other disaccharides such as sucrose and maltose. In addition, in view of the uses for foods, it is expected to use the cellobiose, for example, as a filler for synthetic sweetening agents because it is non-calorific and low sweet-tasting.

(2) Description of Prior Art

As the method to prepare cellobiose, only methods using the starting material of cellulose have hitherto been known. The methods are exemplified by acidolysis of cellulose and enzymatic decomposition of cellulose. In the former method, cellulose is subjected to acetolysis to produce cellobioseoctaacetate and it is then converted into cellobiose by deacetylation (A. N. Pereira at al., Methods Enzymol., 160, 26 (1988)). In the latter method, cellobiose is directly produced from cellulose by treating cellulose with a cellulose-hydrolyzing enzyme of cellulase (Hajime Taniguchi, Nippon Nogeikagaku Kaishi, 63, 1133 (1989)).

In both the foregoing methods, cellobiose is prepared as a decomposition product of cellulose. Incidentally, cellulose is contained as the main component of cell walls of plants, however, it does not exist singly but it exists in the form of mixtures with hemicellulose, lignin and so forth. Accordingly, when cellulose is used as a starting material in the foregoing conventional methods, it is necessary that the hemicellulose and lignin must be removed beforehand from the cellulosic starting material by a suitable method such as alkali treatment, which fact causes to raise the cost of starting material. In addition, because a strong acid is used for the reaction in the acidolysis method, the application to foods is difficult in view of hygienic or safety problem. Meanwhile, there is a problem in the method of enzymatic decomposition that no cellulase which is sufficiently active to cellulose can be obtained. Owing to these reasons, there is proposed at present none of suitable method to produce a large quantity of cellobiose at low cost.

BRIEF SUMMARY OF THE INVENTION

The inventors of the present application have carried out extensive investigation in order to develop a novel method for preparing a large quantity of cellobiose at low cost and in high yields with eliminating the disadvantages inherent in the conventional methods. As a result, it was found out that cellobiose can be prepared in high yields without difficulty by using sucrose as a starting material so as to reduce the cost of raw material and by allowing the three enzymes, in combination, of sucrose phosphorylase, glucose isomerase and cellobiose phosphorylase in the presence of orthophosphate. The present invention has been thus accomplished on the basis of this novel finding.

That is, in the first place, the present invention provides a method for preparing cellobiose which is characterized in that sucrose is treated with sucrose phosphorylase, glucose isomerase and cellobiose phosphorylase in the presence of orthophosphate.

In the next place, the present invention provides a method for preparing cellobiose which comprises:

(1) a step to treat sucrose with sucrose phosphorylase in the presence of orthophosphate to produce fructose and glucose-1-phosphate;

(2) a step to treat the fructose obtained in the step (1) with glucose isomerase to produce glucose;

(3) a step to treat the glucose obtained in the step (2) and the glucose-1-phosphate obtained in the step (1) with cellobiose phosphorylase to produce cellobiose and orthophosphate; and (4) a step to recover at least a part of cellobiose from the reaction mixture in the step (3) and to recycle at least a part of the remaining reaction mixture containing orthophosphate to the step (1).

BRIEF DESCRIPTION OF THE DRAWING

These and other objects and features of the invention will become more apparent from the following description taken in connection with the accompanying drawing in which.

DETAILED DESCRIPTION OF THE INVENTION

Figure 1:
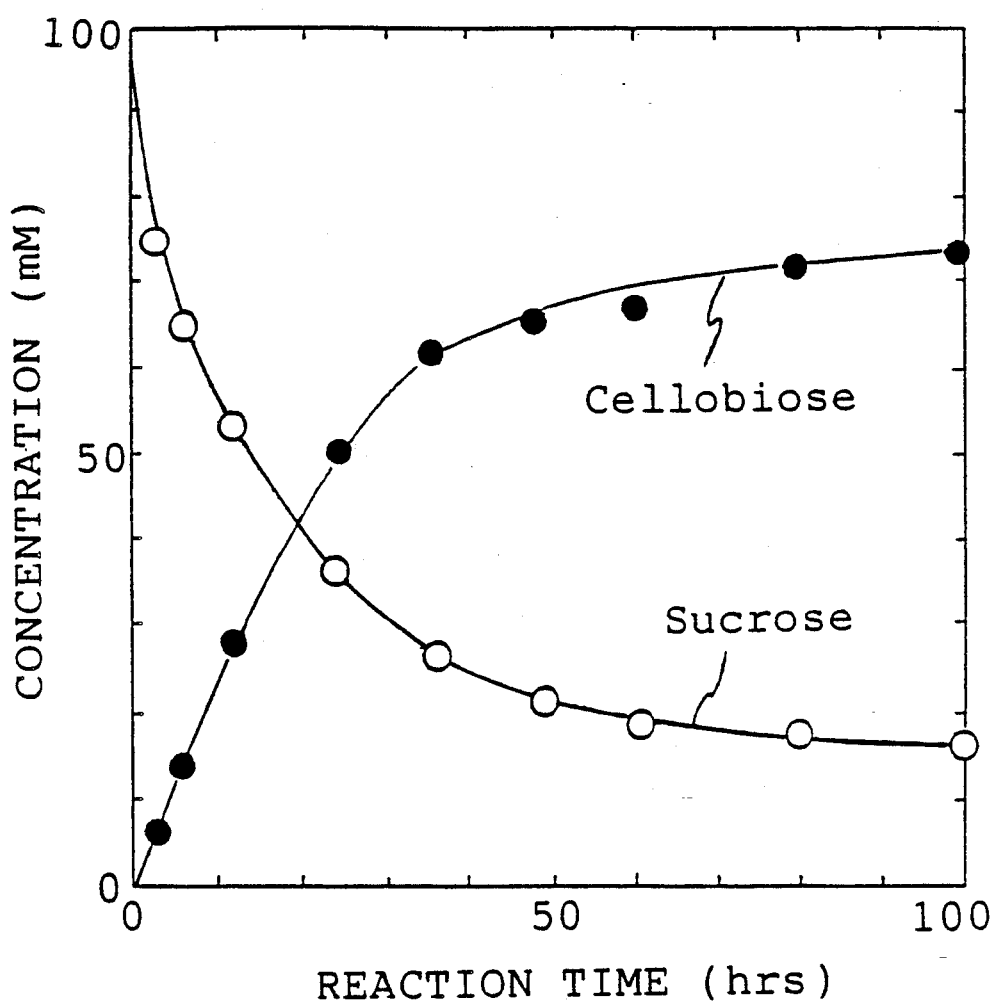
FIG. 1 is a graphic chart showing the change in concentrations of cellobiose and sucrose with the passage of time in the following Example 1.

The sucrose used as the starting material in the method of the present invention is a disaccharide which consists of one molecule of glucose and one molecule of fructose connected by $\alpha$-1, $\beta$-2 linkage. In this method, any of the naturally occurring sucrose and chemically synthesized one can be used. It is also possible to use molasses as a source of starting sucrose without any treatment.

As stated in the foregoing paragraphs, the first invention is a method for preparing cellobiose in which sucrose is treated with sucrose phosphorylase, glucose isomerase and cellobiose phosphorylase in the presence of orthophosphate. This treatment with enzymes is carried out in a suitable aqueous solution such as imidazole-hydrochloric acid buffer solution or phosphate buffer solution.

The enzymes used in this method are well-known ones which are commercially available enzymes or those prepared by the cultivation of enzyme-producing micro-organisms. The enzymes can be employed in any forms such as refined products, crude products, immobilized enzymes prepared by known immobilization method, or microorganisms containing the relevant enzymes. The use quantities of these enzymes are not limited and can be determined arbitrarily, however, it is generally 0.1 unit or more, preferably 200 units or more, per 1 mole of the starting material of sucrose. The unit representing the quantity of enzyme is defined according to the method as described in Preparation Example in the latter part of this specification.

The orthophosphates used in the enzymatic treatment system include ordinary inorganic phosphoric acid as well as other phosphates such as sodium dihydrogenphosphate, potassium dihydrogenphosphate, disodium hydrogenphosphate, dipotassium hydrogenphosphate, trisodium phosphate and tripotassium phosphate, and phosphate buffer solution. The quantity of the above orthophosphates to be used is not limited, however, it is generally 0.001 mole or more, preferably from about 0.01 mole to about 1.5 moles, per 1 mole of the starting material of sucrose. The concentration of sucrose is 0.1 wt.% or higher, preferably 1 wt.% or higher.

The reaction temperatures for the enzymatic treatment must be in the range in which enzyme is not inactivated. It is generally in the range of about 20° C. to 60° C. The pH value of reaction system may also be in the range in which enzyme is not inactivated. That is, the pH is generally in the range of about 5 to 8, preferably about 6 to 7.5. The reaction time is not especially limited, however, it is generally in the range of several hours to several hundred hours and the reaction is to be ceased at the maximum point in view of the formation of cellobiose.

After enzymatic treatment, cellobiose is separated from the reaction mixture and it is refined through appropriate methods. Because enzymes are contained in the treated solution in the above method, the enzymes are firstly inactivated generally by heating the reaction mixture, and cellobiose is then separated from the treated solution by a suitable separation method. In this step, if the sucrose in the reaction mixture hinders the separation, it is decomposed beforehand by using a suitable enzyme. For example, after decomposing unreacted sucrose by adding invertase to the reaction mixture, cellobiose can be refined by a method such as activated carbon column chromatography. Incidentally, for the separation of cellobiose from the reaction mixture, there is a method to precipitate cellobiose selectively utilizing the difference in solubility.

The second invention is a method to prepare cellobiose which is characterized in the following four steps of (1) to (4)

(1) a step to treat sucrose with sucrose phosphorylase in the presence of orthophosphate to produce fructose and glucose-1-phosphate;

(2) a step to treat the fructose obtained in the step (1) with glucose isomerase to produce glucose;

(3) a step to treat the glucose obtained in the step (2) and the glucose-1-phosphate obtained in the step (1) with cellobiose phosphorylase to produce cellobiose and orthophosphate; and (4) a step to recover at least a part of cellobiose from the reaction mixture in the step (3) and to recycle at least a part of the remaining reaction mixture containing orthophosphate to the step (1).

The enzymatic treatment in the above steps is generally carried out in a proper aqueous solution such as imidazolehydrochloric acid buffer solution or phosphate buffer solution. The enzymes used herein are known ones which may be commercially available enzymes or those obtained from the cultivation of enzyme-producing microorganisms. The enzymes can be employed in any forms such as refined products, crude products, immobilized enzymes prepared by known immobilization method, or microorganisms containing the above enzymes.

The quantity of enzyme to be used in each step is not limited and can be determined arbitrarily, however, it is generally 0.1 unit or more, preferably 200 units or more, per 1 mole of each of sucrose, fructose or glucose as the reaction material in each step. The unit representing the quantity of enzyme is defined according to the method which is described in the following Preparation Example.

The orthophosphates used in the step (1) include ordinary inorganic phosphoric acid as well as other phosphates such as sodium dihydrogenphosphate, potassium dihydrogenphosphate, disodium hydrogenphosphate, dipotassium hydrogenphosphate, trisodium phosphate and tripotassium phosphate, and phosphate buffer solution. The quantity of the orthophosphate to be used is not limited, however, it is generally 0.001 mole or more, preferably from about 0.01 mole to about 1.5 moles, per 1 mole of the starting material of sucrose. The concentration of sucrose used in the step (1) is 0.1 wt.% or higher, preferably 1 wt.% or higher.

The enzymatic treatment in each step is carried out at temperatures in which enzyme is not inactivated. It is generally in the range of 20° C to 80° C, and preferably in the range of about 20° to 60° C. in the step (1), in the range of about 20° to 80° C. in the step (2) and in the range of about 20° to 60° C. in the step (3). The pH value of reaction system must also be in the range in which enzyme is not inactivated. That is, the pH is generally in the range of about 5 to 8, preferably about 6 to 7.5 in any step. The reaction time is not especially limited, however, it is generally in the range of several hours to several hundred hours and the reaction may be ceased at the maximum point in view of the yield of cellobiose.

In the above-described method of the present invention, sucrose is treated with sucrose phosphorylase to obtain fructose and glucose-1-phosphate, and the obtained fructose and glucose-1-phosphate are separated and recovered in the step (1). In the next step (2), this fructose is treated with glucose isomerase to obtain glucose. The obtained glucose is then recovered from the reaction mixture, and in the step (3), the glucose obtained in the step (2) and the glucose-1-phosphate obtained in the step (1) were treated with cellobiose phosphorylase to obtain cellobiose and orthophosphate. In the final step (4), at least a part of cellobiose is recovered as the aimed product of the present invention and at least a part of orthophosphate recovered from the step (3) is returned to the foregoing step (1), thereby attaining the recycling of orthophosphate. Owing to the recycling of orthophosphate, cellobiose can be prepared efficiently.

In each of the above steps (1) to (3) of the second invention, it was confirmed by the present inventors that the activity of enzyme in each step is not influenced by reaction materials, products or enzymes in any other step. In other words, the enzymatic reaction in each step is not influenced by the coexistence of reaction materials, products or enzymes of different steps. Accordingly, in a preferable method, the foregoing three kinds of enzymes are immobilized to separate fixed beds or to the same fixed bed by means of a known immobilizing method such as lattice type entrapping method, microcapsule type entrapping method or carrier-attaching method. By using immobilized enzymes, the above steps (1) to (3) can be carried out continuously. More particularly, the above three kinds of enzymes are preferably immobilized to the same fixed bed in the order of sucrose phosphorylase, glucose isomerase and cellobiose phosphorylase; and sucrose and orthophosphate are continuously fed to this fixed bed system, thereby obtaining a reaction mixture containing cellobiose and orthophosphate. The ortho-phosphate can be reused by recycling at least a part of the obtained orthophosphate to the starting material and the yield can be further raised by recycling also the unchanged sucrose.

In this method, the reaction conditions for the above three kinds of enzymes become the same as a matter of course. However, the optimum temperatures of the three kinds of enzymes used in the present invention are not always the same. For example, the reaction temperature of glucose isomerase used in the step (2) is preferably a little higher than those of the other two kinds of enzymes. Accordingly, it is most preferable that the foregoing three kinds of enzymes are separately immobilized to different fixed beds corresponding to steps (1) to (3), respectively, by a known immobilizing method, and the temperature of each fixed bed is adjusted to the optimum temperature of each enzyme; and the reaction mixture from the preceding fixed bed is fed to the next fixed bed and recycled, in other words, the starting material of sucrose and orthophosphate are continuously fed to the fixed bed of the step (1), the reaction mixture of the step (1) is then fed to the fixed bed of the step (2) and so forth. By the way, at least a part of cellobiose is recovered from the reaction mixture obtained from the fixed bed of step (3) containing cellobiose and orthophosphate and at least a part of orthophosphate is reused as the material for the step (1). More particularly, the reaction mixture obtained from the fixed bed of step (3) is recycled intact to the fixed bed of step (1) and a part of this recycled solution is taken out continuously or intermittently and cellobiose and orthophosphate are separated by a suitable method. It is not necessary to inactivate enzyme because any enzyme is of course not contained. Unchanged sucrose, fructose and glucose are contained in this recycled solution, and if they hinder the separation of cellobiose, they are previously removed by appropriate enzyme for decomposition, for example, the sucrose is decomposed by invertase as described in the foregoing paragraph, and after that cellobiose can be obtained through a suitable separation means such as activated carbon chromatography. If the sucrose and the like do not hinder the separation of cellobiose, it is of course not necessary to decompose them. The foregoing method utilizing the difference in solubility can be used for the separation of cellobiose. The remaining solution after the separation of cellobiose is recycled to the step (1) because it contains orthophosphate. According to the above description, each preparation step can be operated at optimum conditions and the orthophosphate can be reused. Therefore, the method of the present invention is quite excellent.

The present invention will be described in more detail with reference to examples. The enzymes used in the examples are prepared through the following method.

PREPARATION EXAMPLE 1

Preparation of Sucrose Phosphorylase

Sucrose phosphorylase (10 mg) obtained from *Leuconostoc mesenteroides* sold by Sigma Chemical Co. was dissolved in 10 ml of 50 mM imidazole-hydrochloric acid buffer solution (pH 7.0). The enzyme activity was 17.5 unit. Furthermore, the reaction with this enzyme was not influenced by the existence of cellobiose and glucose.

The unit of enzyme activity of the above sucrose phosphorylase was defined such that 1 unit was the quantity of enzyme which produced 1 $\mu$ mole of glucose-1-phosphate and equivalent mole fructose per 1 minute at pH 7.0 in the presence of 10 mM sucrose and 10 mM orthophosphate at 37° C.

PREPARATION EXAMPLE 2

Preparation of Glucose Isomerase

Crude enzyme of glucose isomerase (1 g) obtained from Streptomyces made by Nagase Biochemicals, Ltd. and sold by Kanto Chemical Co., Ltd. was suspended in 20 ml of 50 mM imidazole-hydrochloric acid buffer solution (pH 7.0) and the dispersion was disrupted by sonication. The treated liquid was centrifuged and ammonium sulfate was added to the supernatant until it became 80% saturation. The solution was further subjected to centrifugation and the precipitate was dissolved in 5 ml of the above-mentioned buffer solution. The enzyme activity of this solution was 7.5 unit. Furthermore, the reaction with this enzyme was not influenced at all by the existence of sucrose, glucose-1phosphate, orthophosphate and cellobiose. The unit of enzyme activity of the above glucose isomerase was defined such that 1 unit was the quantity of enzyme which produced 1 $\mu$ mole of glucose per 1 minute at pH 7.0 from 10 mM fructose at 37° C.

PREPARATION EXAMPLE 3

Preparation of Cellobiose Phosphorylase

Cultured cell body (10 g in wet weight) of *Cellvibrio gilvus* was suspended in 50 ml of 50 mM phosphate buffer solution (pH 7.0) and it was disrupted by sonication. The treated liquid was centrifuged and ammonium sulfate was added to the supernatant until it became 35% saturation and it was further centrifuged to obtain a supernatant. Ammonium sulfate was added to this supernatant until it became 60% saturation, which was followed by centrifugation and the obtained precipitate was dissolved in 20 ml of the above-mentioned phosphate buffer solution. Adsorption was carried out by passing the solution through DEAE-Toyopearl column (1.5 cm dia. ×15 cm) which had been equilibrated with the same buffer solution. The column was then washed with the same buffer solution and protein was eluted with the linear gradient of 0.15 to 0.25 M NaCl. Active fractions were collected and ammonium sulfate was added to the collected liquid until it became 60% saturation and precipitate was collected by centrifugation. The precipitate was dissolved in 10 ml of 50 mM imidazolehydrochloric acid buffer solution (pH 7.0) to obtain cellobiose phosphorylase. The activity of this enzyme was 42.5 unit and the reaction with this enzyme was not influenced by the existence of sucrose and fructose.

The unit of enzyme activity of the above cellobiose phosphorylase was defined such that 1 unit was the quantity of enzyme which produced 1 $\mu$ mole of orthophosphate and equivalent mole of cellobiose per 1 minute at pH 7.0 in the presence of 10 mM glucose-1-phosphate and 10 mM of glucose at 37° C.

EXAMPLE 1

Sucrose, phosphate buffer solution and three kinds of enzymes were added to 50 mM imidazole-hydrochloric acid buffer solution (pH 7.0) to make up a feed mixture in concentrations of 100 mM sucrose, 10 mM phosphate buffer, 0.26 unit/ml sucrose phosphorylase, 0.034 unit/ml glucose isomerase and 0.29 unit/ml cellobiose phosphorylase. The thus prepared feed mixture was allowed to react at 37° C. and the concentrations of cellobiose and sucrose were measured with the passage of time. The changes in concentration of them are plotted in FIG. 1.

As a result, more than 50% of sucrose was converted into cellobiose after 24 hours and more than 70% of sucrose was finally converted into cellobiose.

EXAMPLE 2

Sucrose, phosphate buffer solution and three kinds of enzymes were added to 10 ml of 50 mM imidazolehydrochloric acid buffer solution (pH 7.0) to make up a feed mixture in concentrations of 200 mM sucrose, 20 mM phosphate buffer solution, 0.22 unit/ml sucrose phosphorylase, 0.058 unit/ml glucose isomerase and 0.21 unit/ml cellobiose phosphorylase. This feed mixture was allowed to react at 37° C. for 120 hours. As a result, the concentration of sucrose was 20.3 mM and the concentration of cellobiose was 147 mM (yield 73.5%). The enzyme was then inactivated by immersing the reaction mixture into boiled water bath for 10 minutes and invertase was added to decompose the remaining sucrose. Fractionation of this reaction mixture was carried out using activated carbon column chromatography, and after concentrating the cellobiose fraction, it was lyophilized to obtain 380 mg of white powder. The yield in the above process was 55%.

EXAMPLE 3

Three columns (0.8 cm dia. ×2 cm) were filled with an anion exchange resin of AMBERLITE IRA 400 (trademark, made by Japan Organo, Ltd.) and the columns were washed with 20 ml of 50 mM imidazole-hydrochloric acid buffer solution (pH 7.0), respectively, and they were named as Column 1, Column 2 and Column 3. 1 ml of sucrose phosphorylase solution prepared in Preparation Example 1 was passed through Column 1 and the Column was then washed with 10 ml of 50 mM imidazole-hydrochloric acid buffer solution (pH 7.0) to obtain immobilized sucrose phosphorylase. 0.1 ml of glucose isomerase solution prepared in Preparation Example 2 was passed through Column 2 and the Column was then washed with 10 ml of 50 mM imidazole-hydrochloric acid buffer solution (pH 7.0) to obtain immobilized glucose isomerase. 0.4 ml of cellobiose phosphorylase solution prepared in Preparation Example 3 was passed through Column 3 and the Column was then washed with 10 ml of 50 mM imidazole-hydrochloric acid buffer solution (pH 7.0) to obtain immobilized cellobiose phosphorylase. A triple column reactor was made by connecting the above Columns 1, 2 and 3 together in series and adjusting Columns 1 and 3 to 37° C. and Column 2, to 50° C. A feed mixture was prepared by adding sucrose and phosphate buffer solution to 50 mM imidazole-hydrochloric acid buffer solution (pH 7.0), in which the concentration of sucrose was 100 mM and that of phosphate buffer solution was 10 mM. 10 ml of this feed mixture was recycled through the triple column reactor at a rate of 5 ml/hour for 60 hours in the order of Column 1 to Column 2 to Column 3 to Column 1. As a result, 73% of the sucrose in the reaction mixture was converted into cellobiose.

According to the present invention as described above, it is possible to prepare easily cellobiose from the starting sucrose in a high yield at low cost by using the combination of three kinds of enzymatic reactions. The rate of conversion, that is the yield, from sucrose to cellobiose in the present invention is as large as more than 70%, which has never been anticipated from known properties of the enzymes used in the present invention.

In addition, when continuous enzymatic reaction is carried out using immobilized enzymes, it is possible to reuse the orthophosphate and it becomes easy to treat with enzymes at optimum temperatures and the efficiency of reaction can be markedly raised.

The cellobiose obtained in the present invention is quite useful in the field of food industries.

What is claimed is:

1. A method for preparing cellobiose which is characterized in that sucrose is treated with sucrose phosphorylase, glucose isomerase and cellobiose phosphorylase in the presence of orthophosphate, wherein the quantities of said three enzymes are 0.1 unit or more per mole of the starting material of sucrose, respectively, the quantity of said orthophosphate is 0.001 mole or more per 1 mole of the starting material of sucrose, the concentration of sucrose of 0.1 wt.% or higher, the reaction temperature is in the range of 20° to 60° C. and the pH value of the reaction system is in the range of about 5 to 8.

2. A method for preparing cellobiose which comprises:
   (1) a step to treat sucrose with sucrose phosphorylase in the presence of orthophosphate to produce fructose and glucose-1-phosphate;
   (2) a step to treat the fructose obtained in the step (1) with glucose isomerase to produce glucose;
   (3) a step to treat the glucose obtained in the step (2) and the glucose-1-phosphate obtained in the step (1) with cellobiose phosphorylase to produce cellobiose and orthophosphate; and
   (4) a step to recover at least a part of cellobiose from the reaction mixture in the step (3) and to recycle at least a part of the remaining reaction mixture containing orthophosphate to the step (1).

3. The method for preparing cellobiose according to claim 2, wherein the quantities of said three enzymes used in said each step is 0.1 unit or more per 1 mole of each of sucrose, fructose or glucose as the reaction starting material in said each step, the quantity of orthophosphates in said step (1) is 0.001 mole or more per 1 mole of the starting material of sucrose, the concentration of sucrose used in said step (1) is 0.1 wt.% or higher, the reaction temperature of said each step is in the range of 20° to 80° C. and the pH value of said each step is in the range of about 5 to 8.

4. The method for preparing cellobiose according to claim 3, wherein said reaction temperature in step (1), (2) and (3) is in the range of 20° to 60° C., and 20° to 80° C. and 20° to 60° C., respectively.

* * * * *